United States Patent
Schutte et al.

(10) Patent No.: US 12,104,148 B1
(45) Date of Patent: Oct. 1, 2024

(54) SYSTEM, APPARATUSES, DEVICES AND METHODS FOR STRAINING A CULTIVATED TISSUE

(71) Applicant: Humacyte, Inc., Durham, NC (US)

(72) Inventors: Robert Schutte, Cary, NC (US); Amanda Elizabeth Basciano, Apex, NC (US); Dustin Cashman, Chapel Hill, NC (US); Joshua McCall, Seattle, WA (US); Laura E. Niklason, Greenwich, CT (US); Heather L Prichard, Wake Forest, NC (US); Justin T. Strader, Durham, NC (US)

(73) Assignee: Humacyte, Inc., Durham, NC (US)

( * ) Notice: Subject to any disclaimer, the term of this patent is extended or adjusted under 35 U.S.C. 154(b) by 60 days.

(21) Appl. No.: 16/875,907

(22) Filed: May 15, 2020

Related U.S. Application Data (60) Provisional application No. 62/849,496, filed on May 17, 2019.

(51) Int. Cl.
  *C12M 3/00* (2006.01)
  *C12M 1/00* (2006.01)
  (Continued)

(52) U.S. Cl.
  CPC ............ *C12M 21/08* (2013.01); *C12M 23/58* (2013.01); *C12M 29/12* (2013.01); *C12M 29/14* (2013.01); *C12M 35/04* (2013.01); *C12M 41/40* (2013.01)

(58) Field of Classification Search
  CPC ...... C12M 21/08; C12M 23/58; C12M 29/12; C12M 29/14; C12M 35/04; C12M 41/40
  See application file for complete search history.

(56) References Cited

U.S. PATENT DOCUMENTS 3,388,574 A * 6/1968 Ignoffo ............... B21D 7/06
  72/21.3
3,606,596 A * 9/1971 Edwards ............. A61M 60/438
  417/474
(Continued)

FOREIGN PATENT DOCUMENTS

| CN | 108440045 | 8/2018 |
| DE | 102016208552 B3 | 4/2017 |

(Continued)

OTHER PUBLICATIONS

CableTiesAndMore. "Braided Cable Sleeving". Dec. 24, 2017. Retrieved Dec. 11, 2021 from WebArchive. https://web.archive.org/web/20171224205238/https://www.cabletiesandmore.com/BraidedSleeving.php.

(Continued)

*Primary Examiner* — William H. Beisner
*Assistant Examiner* — Danielle B Henkel
(74) *Attorney, Agent, or Firm* — COOLEY LLP (57) ABSTRACT

Embodiments of the present disclosure are directed to apparatuses and methods for a pulsing system which can be configured to provide pressure pulses to a fluid communication tube to/from a bioreactor (for example). Such a system may comprise one or more of, and preferably a plurality of a pulsing motor, a compression plate, one or more fluid communications tubes comprising a biomedia fluid tube configured to direct biomedia fluid into and out of one or more bioreactors, and/or an intra-luminal fluid tube configured to direct intra-luminal fluid through a mandrel tube provided in each bioreactor, and one and/or another of a cam, gearing, and/or actuator configured to repetitively moving the compression plate so as to repetitively compress and release at least a portion of a respective intra-luminal fluid tube for a respective bioreactor to effect a temporary (Continued)

pressure increase (distension or strain) in a respective mandrel-tube according to the predetermined time period.

12 Claims, 8 Drawing Sheets

(51) Int. Cl.
  *C12M 1/34* (2006.01)
  *C12M 1/42* (2006.01)

(56) References Cited

U.S. PATENT DOCUMENTS

| | | | | |
|---|---|---|---|---|
| 4,519,754 A * | 5/1985 | Minick | ............... | F04B 43/1284 |
| | | | | 417/477.11 |
| 4,925,376 A * | 5/1990 | Kahler | ................ | F04B 43/1284 |
| | | | | 417/477.11 |
| 5,447,417 A * | 9/1995 | Kuhl | ................... | F04B 43/1284 |
| | | | | 417/477.11 |
| 5,470,744 A | 11/1995 | Astle | | |
| 5,547,329 A | 8/1996 | Hirai et al. | | |
| 5,823,930 A * | 10/1998 | Runge | ................ | A61M 60/853 |
| | | | | 600/16 |
| 6,129,428 A | 10/2000 | Helwig et al. | | |
| 6,475,776 B1 | 11/2002 | Higuchi | | |
| 7,878,786 B2 * | 2/2011 | Yost | ...................... | C12M 21/08 |
| | | | | 425/72.1 |
| 10,085,829 B2 * | 10/2018 | Soletti | ................. | D01D 5/0084 |
| 11,959,060 B1 | 4/2024 | Prichard et al. | | |
| 2004/0219659 A1 | 11/2004 | Altman et al. | | |
| 2004/0241835 A1 | 12/2004 | Hutmacher et al. | | |
| 2005/0009178 A1 * | 1/2005 | Yost | ...................... | C12M 21/08 |
| | | | | 435/399 |
| 2005/0069401 A1 | 3/2005 | Malin | | |
| 2005/0084955 A1 | 4/2005 | Tamaoki et al. | | |
| 2008/0032278 A1 * | 2/2008 | Jones | ..................... | A61F 2/062 |
| | | | | 435/402 |
| 2008/0220506 A1 * | 9/2008 | Yost | ....................... | C12M 25/14 |
| | | | | 435/283.1 |
| 2008/0234806 A1 * | 9/2008 | Dancu | ................... | G09B 23/28 |
| | | | | 435/375 |
| 2009/0042293 A1 | 2/2009 | Hata et al. | | |
| 2010/0105138 A1 | 4/2010 | Dodd et al. | | |
| 2011/0207209 A1 * | 8/2011 | Hammons | ............. | C12M 23/42 |
| | | | | 435/303.1 |
| 2011/0319823 A1 * | 12/2011 | Bojan | ............... | A61M 5/14212 |
| | | | | 33/833 |
| 2012/0028234 A1 * | 2/2012 | Guertin | .................. | C12M 23/14 |
| | | | | 435/395 |
| 2012/0251275 A1 | 10/2012 | Malin | | |
| 2013/0109007 A1 | 5/2013 | Akra et al. | | |
| 2013/0119284 A1 * | 5/2013 | Fukano | .................. | F16K 7/045 |
| | | | | 251/7 |
| 2018/0016540 A1 | 1/2018 | Sekine et al. | | |
| 2018/0058437 A1 * | 3/2018 | Eilers | ................ | A61M 60/554 |
| 2018/0371394 A1 | 12/2018 | Ho et al. | | |
| 2020/0392449 A1 | 12/2020 | Griffin et al. | | |
| 2021/0207073 A1 | 7/2021 | Tanabe et al. | | |

FOREIGN PATENT DOCUMENTS

| | | |
|---|---|---|
| JP | 2006149232 | 6/2006 |
| JP | 2018139615 A | 9/2018 |
| WO | WO-2012170878 A2 | 12/2012 |

OTHER PUBLICATIONS

Discussion of servomotors and braking systems; ResearchGate. 2013. Retrieved Dec. 11, 2021.

* cited by examiner

SYSTEM, APPARATUSES, DEVICES AND METHODS FOR STRAINING A CULTIVATED TISSUE

RELATED APPLICATIONS

This disclosure claims benefit of and priority to U.S. provisional patent application No. 62/849,496, filed May 17, 2019. The entire disclosure, in its entirety, is herein incorporated by reference.

BACKGROUND

There is a considerable need for tissue, e.g., vascular grafts, when the patient's own tissue is unavailable (e.g., damaged, diseased). When autologous tissue is not available, often times synthetic material is used (e.g., synthetic polytetrafluoroethylene (PTFE) for blood vessels). Other types of grafts, such as decellularized bovine tissue, and human allograft tissue, for example, from cadavers, can be used, but are prone to problems (e.g., in the case of blood vessels, aneurysm, calcification, and thrombosis). Thus, there is a need in the art for devices, systems, and methods configured to produce cost-effective tissue engineered constructs that can function long term, with minimal to no side effects, in vivo.

SUMMARY OF SOME OF THE EMBODIMENTS OF THE DISCLOSURE

Exemplary embodiments of the present disclosure are directed to systems, apparatuses, and methods for cultivating and mass producing tissue for use in humans/mammals.

Accordingly, in some embodiments, a tissue cultivating system is provided and comprises a plurality of bioreactors, each configured to cultivate tissue and receive one or more fluids via one or more fluid communication tubes, each fluid configured to aid in cultivating tissue. In some embodiments, the system also includes a pulsing system.

Such embodiments may include one and/or another (e.g., a plurality of, and in some embodiments, all of) of the following additional features, structure, step, functionality, and/or clarifications (as may apply), which corresponds to yet further embodiments of the present disclosure:
  the pulsing system may be configured to provide repetitive pressure-pulses to one or more of the bioreactors;
  each bioreactor includes a mandrel tube, and the pulsing system may be configured to provide the repetitive pressure pulses to each mandrel-tube;
  one or more fluid communications tubes comprising a biomedia fluid tube configured to direct biomedia fluid into and out of one or more bioreactors and/or an intra-luminal fluid tube configured to direct intra-luminal fluid through a mandrel tube provided in each bioreactor; and
  functionality to establish tissue distension, which may include establishing a pressure differential between the intra-luminal fluid and the biomedia fluid, such as, for example, including
    a motor, a compression plate, and one and/or another of a cam, gearing, and/or actuator configured to repetitively moving the compression plate so as to repetitively compress and release at least a portion of a respective fluid tube (e.g., intra-luminal fluid tube) for a respective bioreactor to effect a temporary pressure increase (e.g., in/on a respective mandrel-tube) according to, for example, the predetermined time period;
    at least one of the motor, cam, gearing, and actuator may be configured to move the compression plate so as to repetitively compress and release at least a portion of a respective fluid tube (e.g., intra-luminal fluid tube) to effect a temporary pressure increase in a respective bioreactor;
    can be tunable to provide a specific pressure increase for a pulse;
  at least one pulse dampener arranged on a supply line for supplying at one or more of the bioreactors and/or one or more of the components, where:
    the dampener can be configured to smooth out variability in the pressure pulses;
    the motor speed may be adjusted to effect a particular pulse frequency; and/or
    the pulse dampener effects pulses with respect to a first fluid communication tube configured to deliver intra-luminal fluid to the mandrel-tube;
  at least one flow restrictor, where:
    the at least one flow restrictor can be configured for operation with respect to a fluid communication tube configured to flow an intra-luminal fluid exiting at least one of the bioreactors;
    the at least one flow restrictor may be configured to control at least one of pressure and flowrate; and
    the at least one restrictor may be configurable to provide different flow restrictor functionality based on a change of at least one of internal diameter, length, and material thereof.

In some embodiments, a pulsing system is provided which can be configured to provide pressure pulses to a fluid communication tube comprising a plurality of a pulsing motor, a compression plate, one or more fluid communications tubes comprising a biomedia fluid tube configured to direct biomedia fluid into and out of one or more bioreactors and/or an intra-luminal fluid tube configured to direct intra-luminal fluid through a mandrel tube provided in each bioreactor, and one and/or another of a cam, gearing, and/or actuator configured to repetitively moving the compression plate so as to repetitively compress and release at least a portion of a respective intra-luminal fluid tube (or other fluid tube) for a respective bioreactor to effect a temporary distention, in some embodiments corresponding to a strain (which can be via, for example, a pressure increase between the intra-luminal and biomedia fluids, which effects an increase in diameter in a respective mandrel-tube) according to the predetermined time period. The additional features/functionality/clarifications noted above are also applicable to these embodiments (yielding yet further embodiments).

In some embodiments, a tissue cultivating method is provided and comprises optionally providing the system according to any of the system embodiments disclosed herein, and flowing one or more fluids through each bioreactor configured to aid in cultivating tissue, wherein at least one of the fluids delivered to each bioreactor may be pulsed.

Such embodiments may include one and/or another (i.e., a plurality of, and in some embodiments, all of) of the following additional features, structure, step, functionality, and/or clarifications, which corresponds to yet further embodiments of the present disclosure:
  the one or more fluids comprise at least an intra-luminal fluid;

each bioreactor includes an internal mandrel tube, and wherein the intra-luminal fluid may be configured to flow within the mandrel-tube;

applying a plurality of pressure pulses (which, in some embodiments, are spaced apart according to a predetermined timing) to the flow of the one or more fluids flowing to the bioreactors;

applying a plurality of spaced apart pressure pulses to the flow of the intra-luminal fluid in each of the mandrel-tubes;

the plurality of pulses are applied via a pulsing system according to any of the disclosed pulsing system embodiments disclosed herein, such that, in some embodiments:

the compression plate may be repetitively moved so as to generate the pressure pulses (i.e., functionality to effect bioreactor distension) or distension of a mandrel; and/or at least one of the motor, cam, gearing, and/or actuator may be adjusted to achieve a desired pressure pulse and/or frequency;

dampening the pressure pulses via at least one dampener, where dampening can be configured to smooth out variability in the pressure pulses.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

The above-noted embodiments will become even more evident by reference to the following detailed description and accompanying drawings.

BRIEF DESCRIPTION OF THE DRAWINGS

The skilled artisan will understand that the drawings of this disclosure are primarily for illustrative purposes and are not intended to limit the scope of inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

Figure 1A:
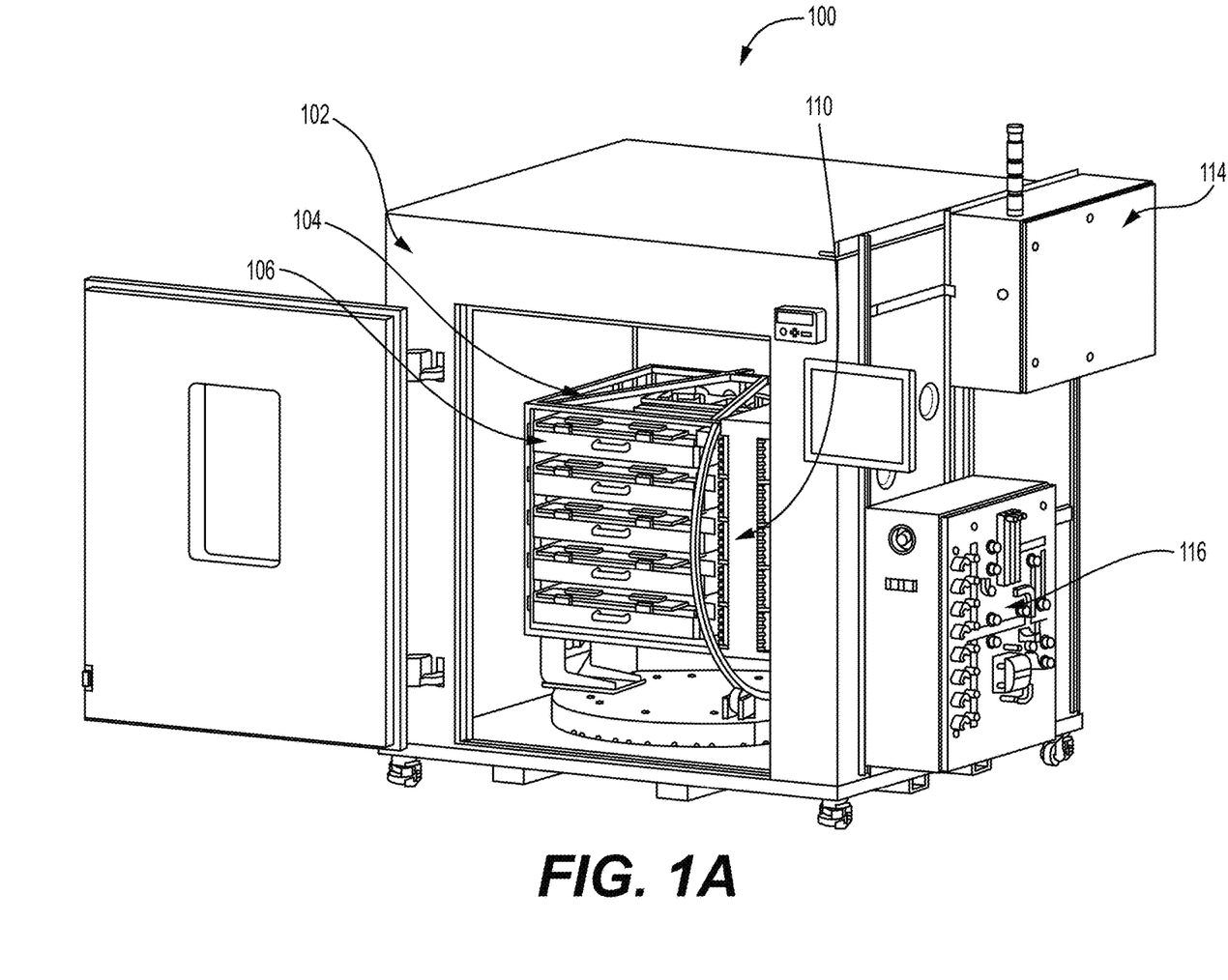
FIGS. 1A-B show an example embodiment of a tissue cultivating system or an incubator used for producing human acellular vessels (HAVs) that can be used to replace diseased or damaged blood vessels in patients, according to some embodiments.
Figure 1B:
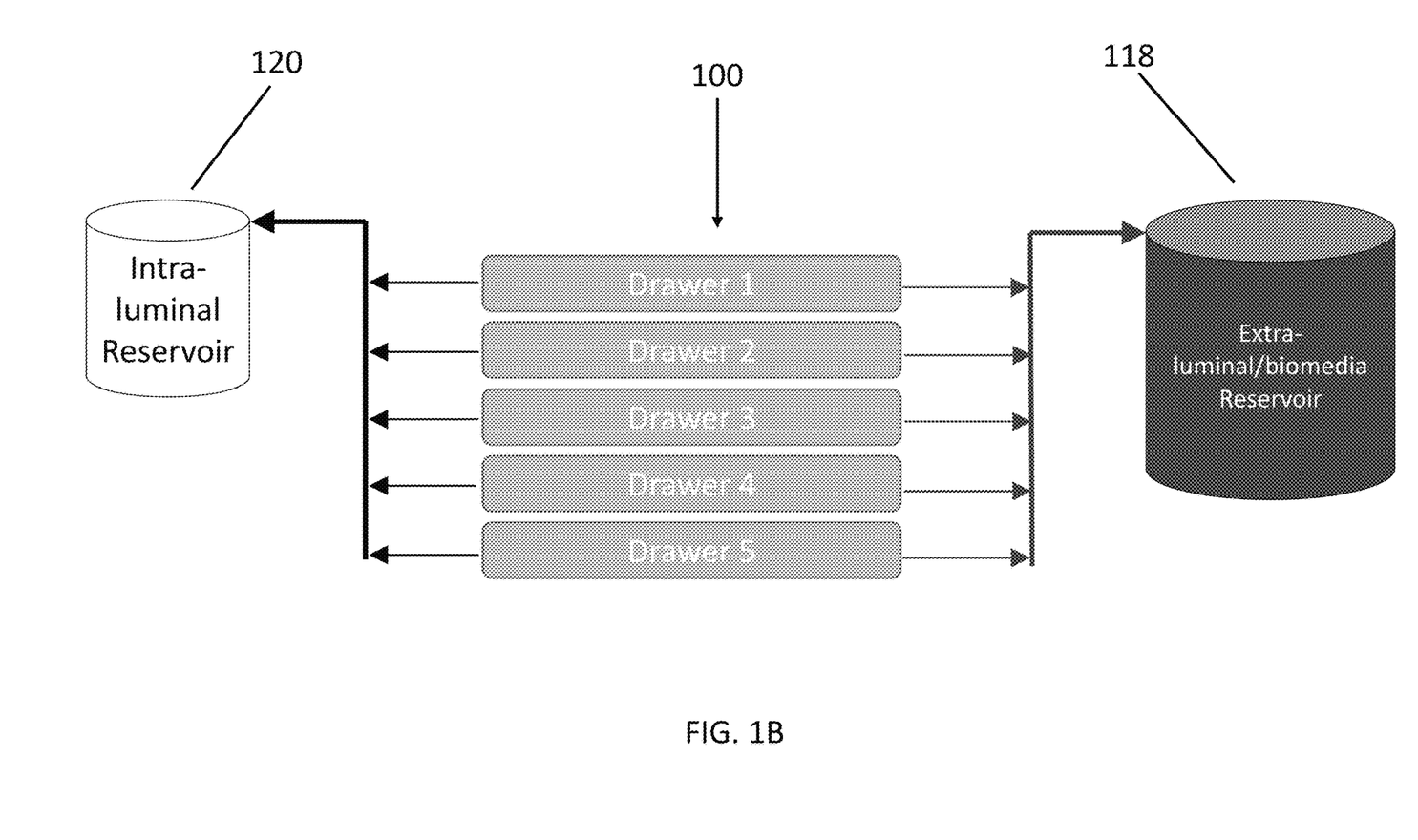

FIGS. 1A, B and C show example embodiments of a tissue cultivating system for incubating/producing tissue. In some embodiments, the system may be used to produce human acellular vessels (HAVs) that can be used to replace diseased or damaged vascular conduits (e.g., blood vessels) in patients. Specifically, and again for example, blood vessels damaged as a result of complications caused by various diseases or caused by trauma can be replaced by HAVs.

As shown, in some embodiments, incubator 100 includes an incubator shell 102, having an access opening, which may include a door, a drawer cage/frame/housing (the terms being used interchangeably) 104 which may be positioned within the incubator shell 102 and may be configured for receiving one or more drawers 106.

The flow of one or more fluids through the drawers 106 can be controlled by a materials/fluid management module (MMM) 110 that may be coupled to the drawer cage 104 (e.g., including being physically attached to the drawer cage) and includes pumps (e.g., peristaltic pumps), sensors (e.g., pressure sensors), tubes/pneumatic connections for facilitating the transfer of fluids within the drawers, electrical components and connections for powering the electronics onboard and/or communicating with controller modules (e.g., external or onboard the incubator), and/or the like. In some embodiments, the incubator 100 may also include an environmental control module or system that facilitates the management of the incubator's environmental characteristics, including but not limited to temperature, humidity, pressure, etc. For example, the system may include incubator connections that facilitate the heating, cooling, humidifying, dehumidifying, increasing pressure and/or decreasing pressure of the incubator.

In some embodiments, the incubator 100 may include a controller module 114 that allows a user to interface with and control the incubator. For example, the controller module 114 may be coupled to the incubator (e.g., including being physically attached to the incubator shell 102) and may include a human machine interface (HMI) that may be configured to allow a user such as an incubator technician, an HAV production worker, etc., to interact with the incubator 100 (e.g., input instructions/data and/or receive data back from the incubator, with the instructions/data including but not limited to incubator status, internal parameters such as pressure, temperature, etc.). In some embodiments, the controller module 114 may also include a programmable logic controller (PLC) that may be configured to facilitate the automation of the HAV production process by the incubator. In some embodiments, the controller module 114 may be configured to communicate wirelessly and/or in a wired setting.

In some embodiments, the incubator 100 may also include a materials management module (MMM) 116 that may be configured to manage the flow of media in the incubator, the drawers, and/or among one or more bioreactors arranged within each drawer, and in some embodiments, between the forgoing and media reservoirs 118 (e.g., intra-luminal reservoir), 120 (extra-luminal fluid, e.g., biomedia). Media reservoirs can be configured with fluid media (which may be referred to, in some embodiments, as biomedia, or intra-luminal fluid, and in some embodiments, a reservoir for each) that may include one or more dissolved gases, elements, nutrients and the like (the fluid may be a liquid or an air/gas flow). The MMM 116 may be coupled (e.g., including being physically attached) to the outside frame of the incubator shell 102, but it can be located anywhere proximate the incubator and may be fluidly connected thereto (as well as fluidly connected to the drawers and/or bioreactors).

Figure 2A:
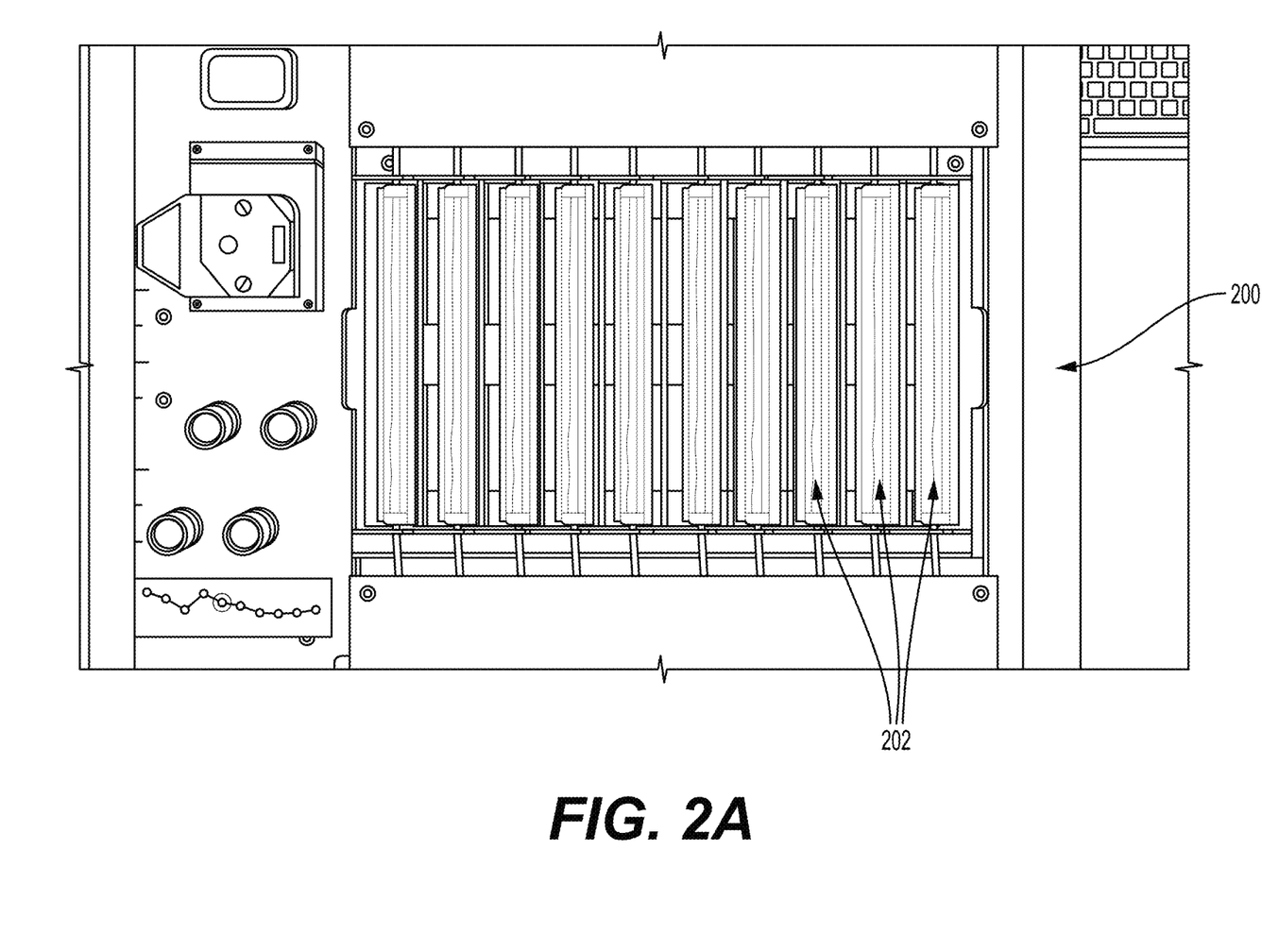
FIG. 2A shows atop view of an embodiment of an incubator drawer, according to some embodiments of the disclosure.

FIG. 2A shows an example embodiment of a drawer. As shown, drawer 200, according to some embodiments, can include one or more (and preferably a plurality) of bioreactor systems ("bioreactors") 202, a pulsing system (not shown), and components associated therewith.

Figure 2B:
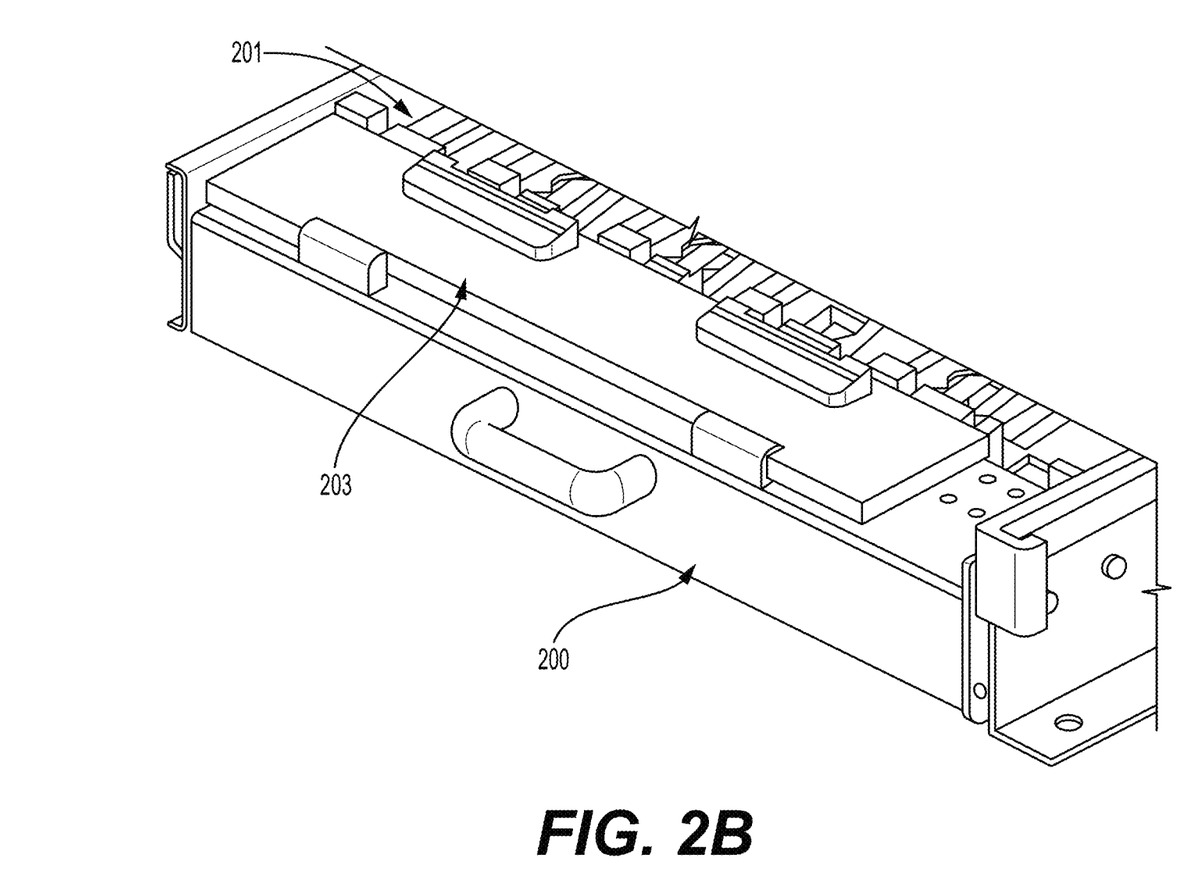
FIG. 2B shows a perspective view of an embodiment of a pulsing system, according to some embodiments of the disclosure.

FIG. 2B shows a portion of a drawer 200 which illustrates some of the components of a pulsing system for establishing tissue distension, according to some embodiments. For example, such a pulsing system effects a pressure increases on fluid supply tubes 201 (either or both of the intra-luminal or "IL fluid", which can be stored in a reservoir, e.g., 120, and biomedia fluid which is provided to each bioreactor outside of the tissue construct), as well as a compression plate 203 which is used to repeatedly compress one or more tubes associated with the bioreactors (e.g., intra-luminal tube).

Figure 2C:
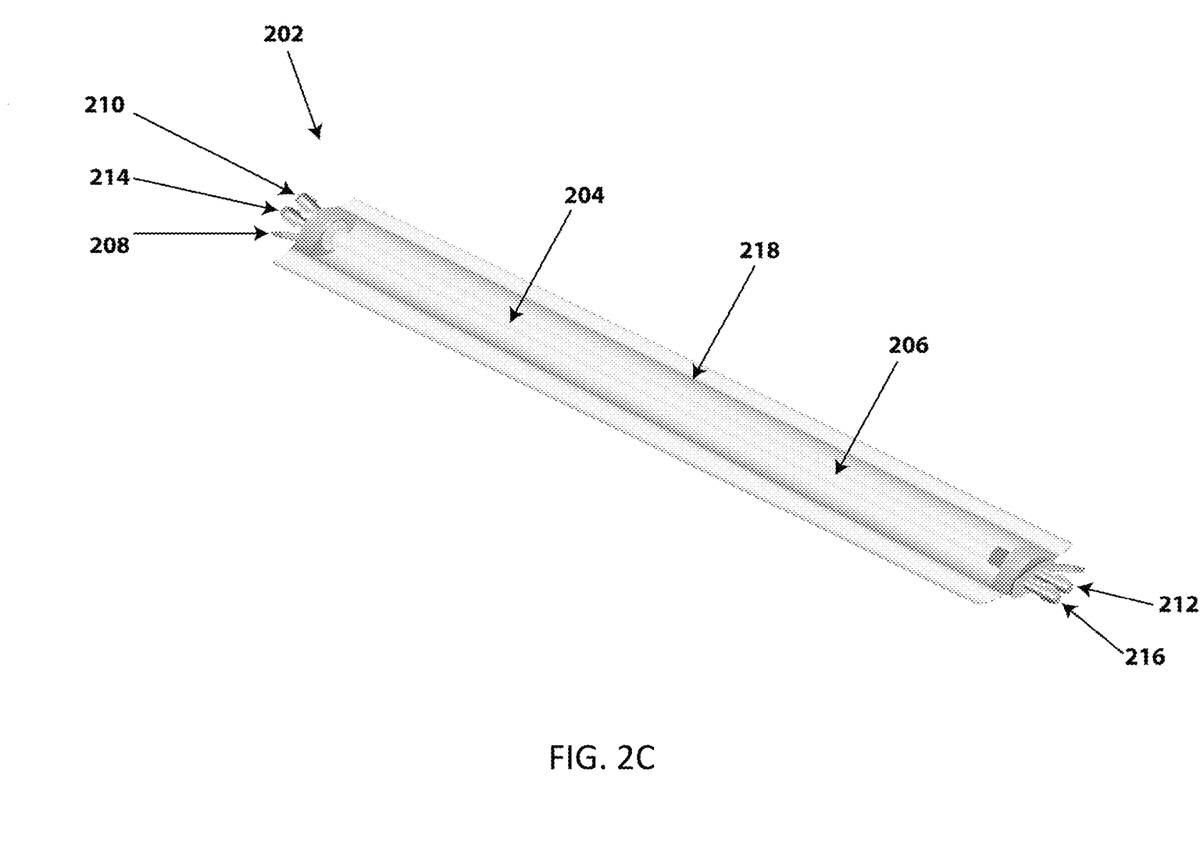
FIG. 2C shows perspective view of a bioreactor according to some embodiments of the disclosure.
Figure 2D:
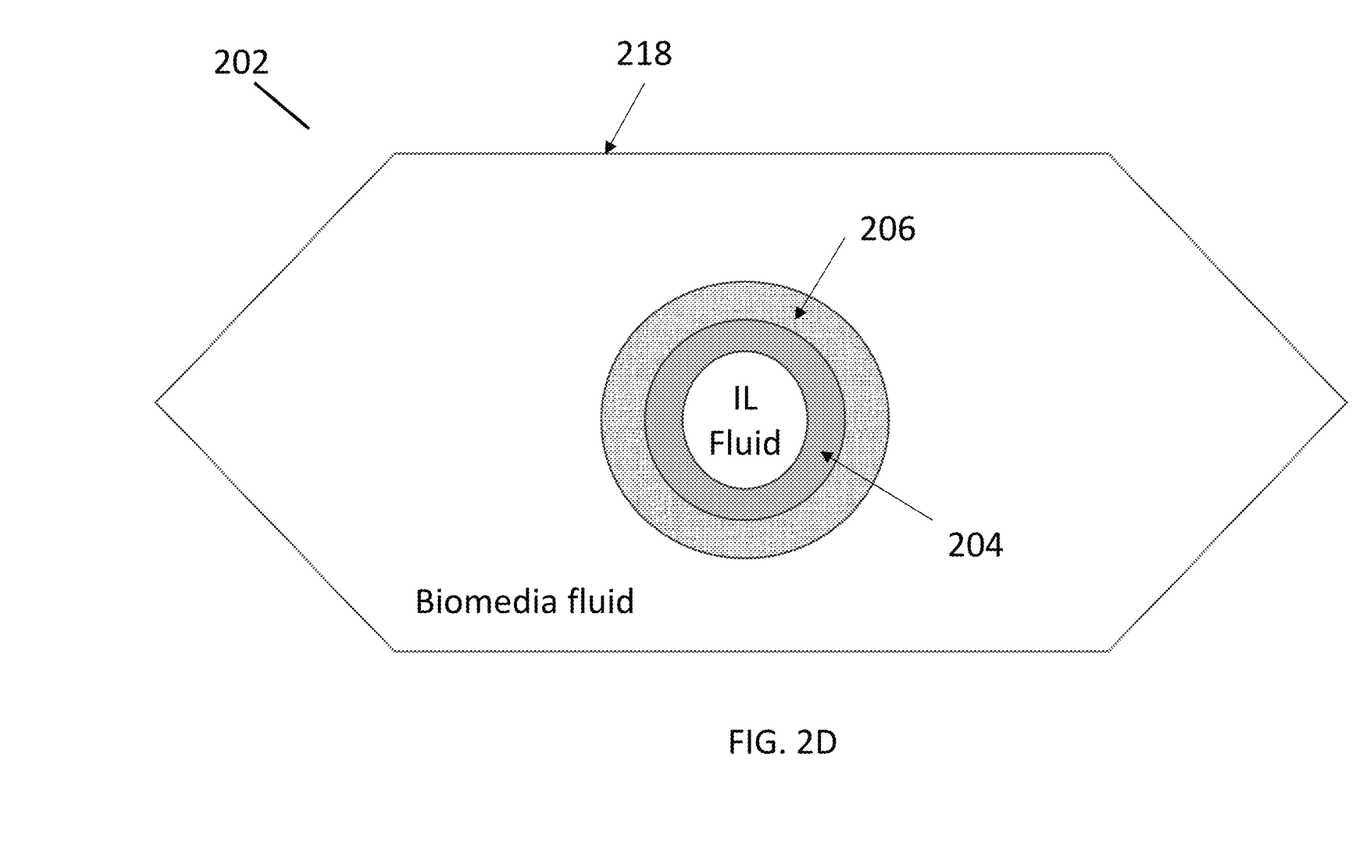
FIG. 2D shows a cross-sectional view of a bioreactor according to some embodiments of the disclosure.

FIGS. 2C-D show a perspective and cross-sectional views of a bioreactor system ("bioreactor"), according to some embodiments, in which tissue (here, HAVs) are produced. In some embodiments, the bioreactor 202 may configured to grow and process tissue, e.g., HAVs 206 (in some embodiments, 206 represents at least one of an HAV and a PGA mesh). Each bioreactor, with reference to producing an HAV, includes a mandrel tube 204 (which can be made from silicone, for example), 220 which are used to support tissue scaffolds, e.g., tubular scaffolds made of polyglycolic acid (PGA) mesh, a biodegradable material onto which cells (e.g., human smooth muscle cells) can be placed in the process of creating an HAV 206.

The mandrel tube 204 may extend between the two ends of the bioreactor, the two ends of the mandrel each having a cuff that may be attached to an end cap (e.g., ultra-low-density polyethylene cap) of the bioreactor. In some embodiments, each bioreactor includes a housing or bag 218 made from ultra-low-density polyethylene.

To this end, in some embodiments, with reference to FIGS. 2C-D, the bioreactor 202 may include a cell injection port 208 configured to receive biological cells for deposition on the scaffolds. Further, each bioreactor 202 may be configured to include one or more inlets and/or outlets for receiving and/or discharging, respectively, various biomedia, fluids and/or gases for treating (growing and/or removing) the deposited cells. For example, a biomedia inlet 210 can be included and configured for receiving a biomedia fluid and a biomedia outlet 212 for expelling the biomedia fluid after the fluid traverses through the bioreactor, washing over, for example, and the scaffold contained within. In some embodiments, the biomedia fluid may include one or more nutrients and/or gases dissolved therein, for use in culturing the deposited cells.

In some embodiments, each bioreactor 202 may also include intra-luminal fluid inlet 214 and outlet 216 for receiving and expelling, respectively, intra-luminal fluids ("IL Fluid", see FIG. 2D) containing one or more dissolved gases, and/or nutrients, etc. For example, an intra-luminal fluid tube running between the intra-luminal fluid inlet 214 and the intra-luminal fluid outlet 216 may direct the intra-luminal fluids to traverse through the mandrel tube 204.

In some embodiments, the incubator disclosed herein includes a plurality of tubes for transporting biomedia, intraluminal fluid, gases and/or the like from reservoirs (for example, 118/120, see FIG. 1B) to at least one of the incubator shell, the drawer cage, one or more of the drawers, and one or more of the bioreactors. With respect to the bioreactors, such fluid/gas communication may be supplied to inlets at ends of the bioreactors, which may then be discharged the same from the bioreactors via the outlets at the other ends of the bioreactors.

The one or more fluids/gases being transported to and/or from at least one of the incubator shell, the one or more drawers and the one or more bioreactors arranged in a drawer, via one or more fluid communication tubes can also include various valves, clamps, and the like so as to selectively at least one of restrict, enable, start, and stop the flow of a liquid or gas flowing through such tube(s). Some embodiments of the present disclosure correspond to the placement of one and/or another of the valves among one and/or another of one or more of the fluid communication tubes.

Further yet, one or more pumps can be included (which may be part of the MMM), so as to provide pressure and/or flowrate to one or more of the fluids being supplied (ultimately) to the bioreactors, controllable, in some embodiments, via a controller/processor.

In some embodiments, a drawer comprising one or more bioreactors may include a system for providing elastic strain to tissue being cultivated. According, in some embodiments, a pulsing system may be provided which may be configured to provide a pulsating pressure (e.g., intermittent, temporary increased pressure) to at least one of the media and intra-luminal fluid flows. In some embodiments, the pulsing system may be associated with respect to at least the intra-luminal fluid flow within the mandrel tubes of the bioreactors. Specifically, the pulsed pressure can be configured so as to vary the diameter of the mandrel tube, which thereby can vary the diameter of each of the scaffold and tissue (e.g., HAV) during the generation of tissue (e.g., HAVs). With respect to the generation of HAVs, such elastic strain establishes tissue distension (as noted above, which such strain is but one way to establish such distension), by, for example, enabling the bioreactor and/or an HAV for example (i.e., tissue) to include elasticity—so as to mimic pressure pulses from a beating heart. In some embodiments, the elasticity of the HAVs may be determined at least in part by the strength (e.g., amplitude) and/or frequency of the pressure pulses propagating through the intra-luminal tubes. For example, the pressure/flow can be, according to some embodiments, to provide between about 0.5% to about 3.0% strain on at least one of the mandrel, the bioreactor, and the HAV. The pulses, in some embodiments, can be spaced apart between about 100 to 250 pulses per minute.

The pulsing system, according to some embodiments, includes one or more compression plates that are operationally coupled to at least one of one or more of the bioreactors, and one or more of the tubes supplying fluid/gas thereto (e.g., a common intra-luminal fluid supply tube for supplying intra-luminal fluid to a mandrel or tubular tissue construct). The plate(s) can be raised and lowered so as to compress/squeeze at least one intra-luminal fluid supply tube, for example (e.g., a tube for supplying one or more bioreactors with intra-luminal fluid to an inner mandrel and/or tubular tissue construct) passing between a side of the plate and a second rigid surface, so as to increase the pressure of fluid/gas within the tube during the time the fluid is squeezed. Alternately, and for another example, two opposed plates moving independently or together can squeeze such a tube arranged therebetween to obtain a desired increase in pressure. Still further, gravity may be used such that a "falling" compression plate "falls" on a fluid tube. Accordingly, as noted above, this functionality can be used to generate the intermittent, pulsating pressure configured to vary the diameters of the mandrel, scaffold supporting the growth of the HAVs (thereby bestowing elasticity to the HAVs).

The pulsing system may include a compression plate (shown as item 203 in FIG. 2B) that produces, upon compressing a fluid communication tube, increased pressure pulses that are delivered, for example, to the intra-luminal fluid flows flowing through the mandrel tube of each bioreactor. The compression plate may be operationally coupled to a drawer (or the incubator shell) and arranged/configured to impact a squeezing effect on an intra-luminal fluid communication tube the compresses the tube as and to generate a pulse to the flow inside the mandrel tube within the bioreactor. In some embodiments, the strength or amplitude of the pressure pulses may be determined at least in part by the height/travel of the at least one plate above the fluid communication tube, to produce a specific "fall" to compress the tube. Alternatively, the compression plate may be operated by at least one of a cam, gearing and actuator (e.g., electric, pneumatic) system which repetitively moves the compression plate back and forth against a second rigid (e.g., affixed) surface (or two moving opposed plates), with the fluid communication tube lying therebetween. The amount of resulting increased pressure, or distension of at least one of the bioreactor, the mandrel, and HAV, can be pre-set/determined, e.g., in some embodiments, by the amount the tube is compressed and spacing of pressure pulses (for example). Thus, and for example, the amount of tube compression/squeezing can be changed by changing the travel of the plate, and/or how close the plate comes to a second plate or an opposed rigid surface.

Figure 3A:
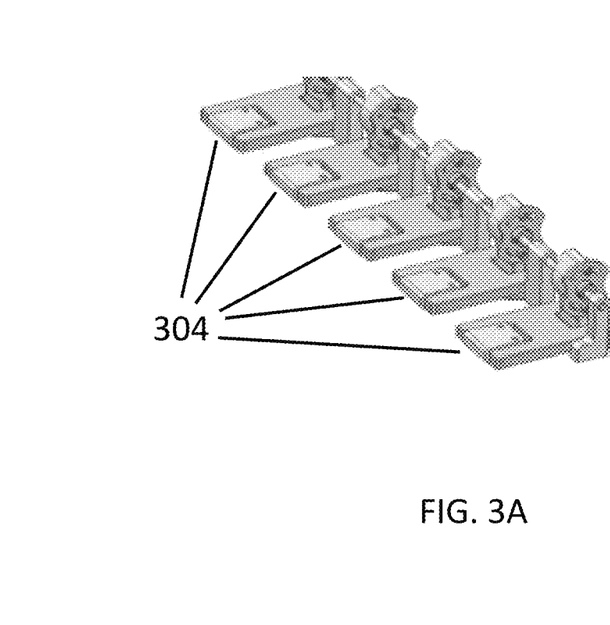
FIGS. 3A-B show view of components of a pulsing system according to some embodiments of the present disclosure.
Figure 3B:
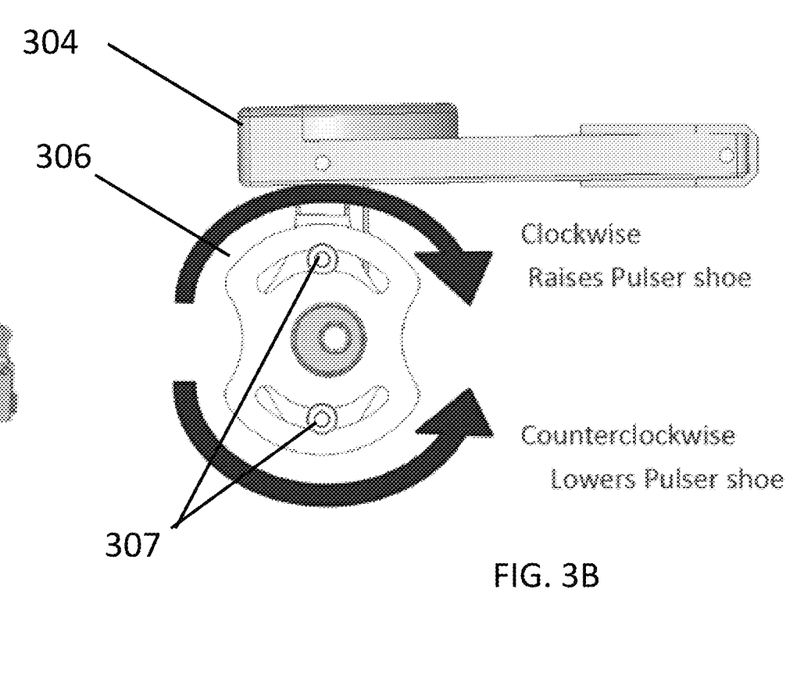

In some embodiments, the pulsing system may include adjustable cam(s) and/or gear(s) which may be coupled to the compression plate(s) (e.g., see item 203, FIG. 2B) and configured to vary the amount the tube can ultimately be compressed, hence the strength/pressure increase of the pulse. Examples of this are shown in FIGS. 3A-B, which show pulsing plate shoes 304 (which drive the compression plate) coupled to rotatable travel adjusters/cams/gears 306 (such terms may be used interchangeably throughout) that are configured to change the amount of travel that the compression plate moves (e.g., upon rotation of an axle powered by a motor, see below). For example, the rotatable travel adjusters 306 may rotate in a direction to raise, and then lower the compression plate(s), and can be changed to increase or decrease the actual travel of the compression plate(s). Other possible gearing, motor spin direction(s), and the like, can be used to effect appropriate pressure increases so desired to effect elastic strain (for example) on a tissue being cultivated.

In some embodiments, the pulsing system may also include a pulsing motor for turning an axle upon which the travel adjusters/cam/gearing may be arranged. To this end, and according to some embodiments, a pulsing period may correspond to the speed of the motor, which effects a particular travel of one or more of compression plates and the generation of the pressure pulses. For example, the pulsing motor may be coupled to the travel adjusters 306 (and/or directly to the compression plate) to cause the compression plate shoes 304 to move/travel via the rotating height adjusters 306 to rotate. In some embodiments, as noted above, the speed and/or timing of the pulsing motor can be used to control the parameters (e.g., strength/amplitude and/or frequency) of the pulsating pressure propagating in the intra-luminal fluids within the mandrel tubes of bioreactors, thereby facilitating the determination of the HAV elasticity by varying the operation of the pulsing motor. Adjustment to the lift of the plate (to change at least one of lift distance and lift timing of compression plate shoes, and therefore the compression plate(s)) can be had by releasing the cam via set-screws 307, and rotating the cam in clockwise or counter-clockwise.

Figures 4A, 4B, 4C:
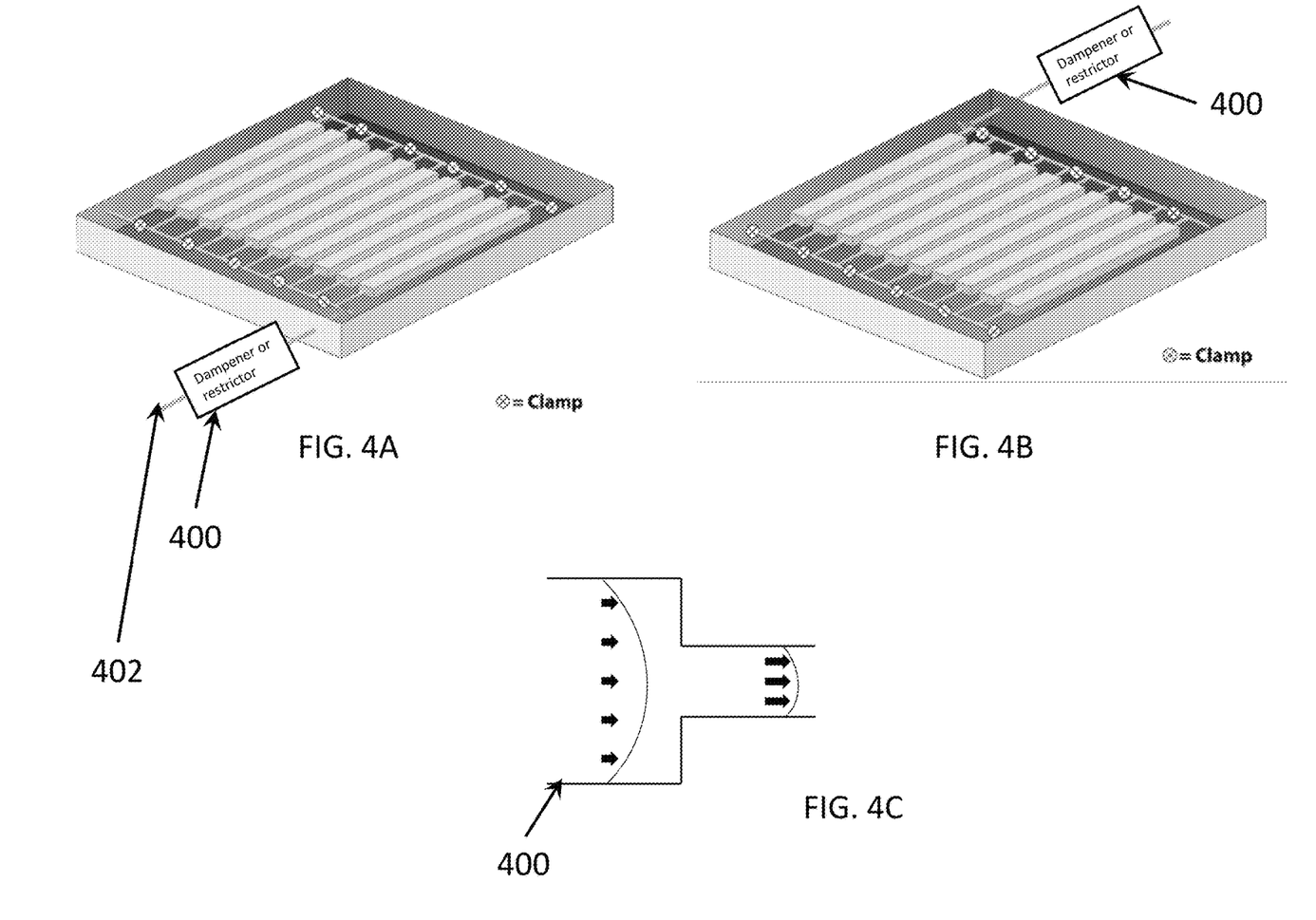
FIGS. 4A-B shows a fluid system for a plurality of bioreactors which includes a pulse dampener and/or flow restrictor component, according to some embodiments of the disclosure.
FIG. 4C shows a cross-sectional view of a flow restrictor component illustrating the functionality thereof, according to some embodiments of the disclosure.

In some embodiments, pressure waves along a fluid flow (in a fluid communication tube) from a pump (and/or pulsing system—see above) can cause variability in the total fluid pressure available. Accordingly, in some embodiments, a pulse dampener 400 can be provided and arranged on a supply or return line (for example) of a fluid communication tube 402 (e.g., the intra-luminal fluid flow), which may be configured to address such variabilities by at least substantially smoothing the pressure variabilities out. FIGS. 4A-B show example illustrations of the use and positioning of pulse dampeners 400 (as well as locations of clamps/valves, such terms used interchangeably, and in some embodiments, perform similar or the same function(s) for example) to regulate variabilities in pressure waves within mandrel tubes of bioreactors within drawers, according to some embodiments of the present disclosure. In some embodiments, as discussed above, serial flow of fluids (such as the intra-luminal fluids, for example) allows each bioreactor to experience at least substantially similar fluid conditions, such as consistent nutrients, metabolites and/or dissolved gas profiles, etc., as a result of, amongst other reasons, at least comparable fluid flow rate in each of the bioreactors (e.g., compared to parallel fluid flows where multiple pumps can be used, leading to different flow rates). To maintain the at least substantially similar fluid conditions amongst bioreactors, in some embodiments, pulse dampeners can be located at intra-luminal fluid inlets or outlets (or both, depending upon the embodiments) of each drawer such that the dampeners can push out against the inlet flow (e.g., when a dampener is arranged with an inlet) and smooth out the flow. In some embodiments, a flow resistor may be provided on a fluid supply/return line that may be configured to maintain a baseline fluidic/hydrodynamic pressure along the paths of a fluid flow (e.g., the intra-luminal fluid flow from the reservoir through exiting the bioreactors). FIG. 4C is a cross-sectional illustration of the functionality of such a flow restrictor according to some embodiments. Such a flow resistor may be positioned along the tube or path leading from intra-luminal outlets of a drawer or bioreactors (for example) to an intra-luminal fluid waste disposal area (which can be the intra-luminal fluid reservoir itself, for example).

Control of various embodiments of tissue cultivating systems disclosed herein, as well as one or more components and/or sub-systems thereof (and the making of HAVs for example) can be accomplished via hardware, software or a combination thereof (e.g., the control module as set out above). When implemented in software, the software code can be executed on any suitable processor or collection of processors, whether provided in a single computer or distributed among multiple computers.

Typically, such systems are controlled by one or more computer programmable processors (either AISC or via software) having one or more applications running thereon which operate one or more (and preferably all) of the pumps, motors, sensors, valves, clamps of the tissue cultivating systems disclosed herein. To this end, and as noted, one or more sensors can be provided to collect information (e.g., sense a condition) for any component and sub-system of the disclosed tissue cultivating systems which allow the controller to perform the cultivating process as so desired.

Such controllers/computers may be embodied in any of a number of forms, such as a rack-mounted computer, a desktop computer, a laptop computer, or a tablet computer (i.e., processor), server, and the like. Additionally, a computer may be embedded in a device not generally regarded as a computer but with suitable processing capabilities, including a Personal Digital Assistant (PDA), a smart phone or any other suitable portable or fixed electronic device. Also, a computer may have one or more input and output devices. These devices can be used, among other things, to present a user interface which can be used to at least one of program, operate, and monitor the embodiments disclosed herein. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such controllers/computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

As noted, control processes described (or at least outlined) herein may be coded as software that is executable on the noted controller or associated one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As noted elsewhere, the disclosed inventive embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses/devices which may further include any and all elements from any other disclosed methods, systems, and devices, including any and all elements corresponding to binding event determinative systems, devices and methods. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Also, some embodiments correspond to systems, devices and methods which specifically lack one and/or another element, structure, and/or steps (as applicable), as compared to teachings of the prior art, and therefore, represent patentable subject matter and are distinguishable therefrom (i.e. claims directed to such embodiments may contain negative limitations to note the lack of one or more features prior art teachings).

All definitions, as defined and used herein, should be understood to control over dictionary definitions, definitions in documents incorporated by reference, and/or ordinary meanings of the defined terms. Any and all references to publications or other documents, including but not limited to, patents, patent applications, articles, webpages, books, etc., presented anywhere in the present application, are herein incorporated by reference in their entirety.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A tissue cultivating system comprising:
a plurality of bioreactors, each bioreactor of the plurality of bioreactors comprising a mandrel tube, each bioreactor configured to cultivate tissue and receive one or more fluids, each fluid configured to aid in cultivating tissue; and
a pulsing system configured to provide pulsed fluid to the mandrel tube of each bioreactor, the pulsing system comprising:
a pulsing motor;
one or more intra-luminal fluid tubes configured to direct intra-luminal fluid through a respective mandrel tube of a respective bioreactor;
at least one compression plate; and
at least one actuator couplable to the pulsing motor and configured to move the at least one compression plate to compress the one or more intra-luminal fluid tubes, the at least one actuator comprising
at least one pulsing plate shoe in actuatable contact with the at least one compression plate, and
an adjustable cam coupled to the at least one pulsing plate shoe,
wherein:
the cam includes at least one set-screw and at least one slot for receiving the at least one set-screw,
the at least one set-screw is configured for rotationally constraining the cam relative to the at least one pulsing plate shoe so as to limit travel of the at least one compression plate to a desired amount, and
constraint of the cam is adjustable by releasing the set-screw, moving the cam to a different position, and then setting the set-screw, the adjustment rotationally constraining the cam to the desired amount so as to effect a desired change in an amplitude of the compression of the one or more intra-luminal fluid tubes,
the at least one compression plate is configured to be repetitively moved by the at least one actuator so as to compress and release the one or more intra-luminal fluid tubes, thereby affecting a pressure change in each mandrel tube for a predetermined time period, and
patency of the one or more intra-luminal fluid tubes is controlled by the amplitude of the compression of the one or more intra-luminal fluid tubes.

2. The tissue cultivating system of claim 1, wherein the pulsing system is configured to repetitively pulse the pulsed fluid to each mandrel tube of each bioreactor.

3. The tissue cultivating system of claim 1, wherein each one of the at least one actuator is configured to move a respective one of the at least one compression plate so as to repetitively compress and release at least a portion of a respective one of the one or more intra-luminal fluid tubes.

4. The tissue cultivating system of claim 1, wherein the pulsing system is configured to be tunable to provide a specific pressure change and/or distension for a pulse.

5. The tissue cultivating system of claim 1, further comprising at least one pulse dampener arranged on a supply line that supplies at least one or more of the bioreactors.

6. The tissue cultivating system of claim 5, wherein the at least one pulse dampener is configured to smooth out variability amongst pulsed fluids.

7. The tissue cultivating system of claim 1, wherein the pulsing motor speed is adjustable to affect a particular pulse frequency.

8. The tissue cultivating system of claim 1, wherein the pulsing system further comprises at least one flow restrictor.

9. The tissue cultivating system of claim 8, wherein the at least one flow restrictor is configured for operation with respect to an output flow of each mandrel tube.

10. The tissue cultivating system of claim 8, wherein the at least one flow restrictor is configured to control at least one of pressure and flow rate.

11. The tissue cultivating system of claim 8, wherein the at least one flow restrictor is configurable to provide variable restrictiveness based on a change of at least one of an internal diameter, a length, and a material thereof.

12. The tissue cultivating system of claim 1, wherein the one or more intra-luminal fluid tubes are compressed between a first planar surface and a second planar surface, the first planar surface being a surface of the at least one compression plate.

* * * * *

UNITED STATES PATENT AND TRADEMARK OFFICE
CERTIFICATE OF CORRECTION

| | | |
|---|---|---|
| PATENT NO. | : 12,104,148 B1 | Page 1 of 1 |
| APPLICATION NO. | : 16/875907 | |
| DATED | : October 1, 2024 | |
| INVENTOR(S) | : Robert Schutte et al. | |

It is certified that error appears in the above-identified patent and that said Letters Patent is hereby corrected as shown below:

On the Title Page

Item (72), Inventors: Lines 6-7:
"Heather L Prichard"
Should read:
-- Heather L. Prichard --

Signed and Sealed this
Eighteenth Day of February, 2025

Coke Morgan Stewart
*Acting Director of the United States Patent and Trademark Office*